US011060097B2

United States Patent
Govindappa et al.

(10) Patent No.: US 11,060,097 B2
(45) Date of Patent: Jul. 13, 2021

(54) IMMUNOTHERAPY METHODS USING ANTI-PD-L1 ANTIBODIES IN COMBINATION WITH EGFR1 TARGETED-TGF-BETA IMMUNOMODULATORY FUSION PROTEINS

(71) Applicant: BIOCON LIMITED, Bangalore (IN)

(72) Inventors: Nagaraj Govindappa, Karnataka (IN); Sreesha P. Srinivasa, Bangalore (IN); Usha Bughani, Bangalore (IN); Reshmi Nair, Bengaluru (IN)

(73) Assignee: BIOCON LIMITED

( * ) Notice: Subject to any disclaimer, the term of this patent is extended or adjusted under 35 U.S.C. 154(b) by 0 days.

(21) Appl. No.: 16/263,157

(22) Filed: Jan. 31, 2019

(65) Prior Publication Data

US 2019/0169621 A1 Jun. 6, 2019

Related U.S. Application Data

(60) Continuation-in-part of application No. 15/795,404, filed on Oct. 27, 2017, now Pat. No. 10,385,348, which is a division of application No. 15/047,062, filed on Feb. 18, 2016, now Pat. No. 9,809,651, which is a division of application No. 14/458,674, filed on Aug. 13, 2014, now Pat. No. 9,340,617, which is a division of application No. 13/799,409, filed on Mar. 13, 2013, now Pat. No. 8,815,247.

(30) Foreign Application Priority Data

Apr. 30, 2012 (IN) .......................... 1689/CHE/2012
Apr. 30, 2012 (IN) .......................... 1690/CHE/2012

(51) Int. Cl.
| | |
|---|---|
| C07K 16/28 | (2006.01) |
| C07K 14/705 | (2006.01) |
| C07K 14/495 | (2006.01) |
| C07K 14/71 | (2006.01) |
| C07K 14/00 | (2006.01) |
| A61K 39/395 | (2006.01) |
| A61K 38/17 | (2006.01) |
| C12N 15/62 | (2006.01) |
| G01N 33/68 | (2006.01) |
| C07K 16/32 | (2006.01) |
| C07K 14/65 | (2006.01) |
| C07K 7/08 | (2006.01) |
| A61K 48/00 | (2006.01) |
| C07K 16/30 | (2006.01) |
| A61K 38/10 | (2006.01) |
| A61K 45/06 | (2006.01) |
| C12N 5/00 | (2006.01) |
| A61K 39/00 | (2006.01) |
| A61K 38/00 | (2006.01) |

(52) U.S. Cl.
CPC .............. *C12N 15/62* (2013.01); *A61K 38/10* (2013.01); *A61K 38/179* (2013.01); *A61K 39/395* (2013.01); *A61K 39/39558* (2013.01); *A61K 45/06* (2013.01); *A61K 48/005* (2013.01); *C07K 7/08* (2013.01); *C07K 14/00* (2013.01); *C07K 14/495* (2013.01); *C07K 14/65* (2013.01); *C07K 14/70532* (2013.01); *C07K 14/70596* (2013.01); *C07K 14/71* (2013.01); *C07K 16/2818* (2013.01); *C07K 16/2863* (2013.01); *C07K 16/2866* (2013.01); *C07K 16/2878* (2013.01); *C07K 16/2887* (2013.01); *C07K 16/30* (2013.01); *C07K 16/32* (2013.01); *C12N 5/0018* (2013.01); *G01N 33/6854* (2013.01); *A61K 38/00* (2013.01); *A61K 2039/505* (2013.01); *A61K 2121/00* (2013.01); *C07K 2317/14* (2013.01); *C07K 2317/24* (2013.01); *C07K 2317/31* (2013.01); *C07K 2317/51* (2013.01); *C07K 2317/515* (2013.01); *C07K 2317/732* (2013.01); *C07K 2319/00* (2013.01); *C07K 2319/02* (2013.01); *C07K 2319/33* (2013.01); *C12N 2500/22* (2013.01)

(58) Field of Classification Search
None
See application file for complete search history.

(56) References Cited

U.S. PATENT DOCUMENTS

| | | |
|---|---|---|
| 7,141,651 B2 | 11/2006 | Gillies et al. |
| 9,452,149 B2 | 9/2016 | Nilsson et al. |
| 2011/0104734 A1 | 5/2011 | Croughan et al. |

FOREIGN PATENT DOCUMENTS

| | | |
|---|---|---|
| RU | 2120475 C1 | 10/1998 |
| WO | WO 1998/33914 | 8/1998 |
| WO | WO200155163 | 8/2001 |

(Continued)

OTHER PUBLICATIONS

Russian Office Action, corresponding to Russian Divisional Patent Application No. 2018117558, issued by the Patent Office of the Russian Federation dated Jan. 29, 2019.

(Continued)

*Primary Examiner* — Elly-Gerald Stoica
(74) *Attorney, Agent, or Firm* — Marianne Fuierer; Olive Law Group, PLLC

(57) ABSTRACT

The present invention provides for a composition and a method for treating a subject afflicted with a cancer, wherein the composition comprises therapeutically effective amounts of: (a) an anti-Programmed Death-Ligand 1 (PD-L1) antibody and (b) a targeted/immunomodulatory fusion protein comprising at least one tumor targeting moiety and at least one immunomodulatory moiety that counteracts the immune tolerance of cancer cells.

4 Claims, 6 Drawing Sheets

Specification includes a Sequence Listing.

(56) References Cited

FOREIGN PATENT DOCUMENTS

| WO | WO 2009/039409 | 3/2009 |
|---|---|---|
| WO | WO2009027471 A1 | 3/2009 |
| WO | WO 2009/114110 | 9/2009 |
| WO | WO 2011/109789 | 9/2011 |
| WO | WO 2012033953 | 3/2012 |
| WO | WO2012147048 A2 | 11/2012 |
| WO | WO2014164427 | 10/2014 |

OTHER PUBLICATIONS

Luo, J. et al. "Comparative metabolite analysis to understand lactate metabolism shift in Chinese hamster ovary cell culture process." Biotechnology and Bioengineering, 2011, vol. 109, No. 1, pp. 146-156.

Birch, J. R. et al. "Antibody production." Advanced Drug Delivery Reviews, vol. 58, No. 5-6, Aug. 7, 2006.

Carton et al. "Codon engineering for improved antibody expression in mammalian cells." Protein Expression and Purification, Academic Press, vol. 55, No. 2, Sep. 8, 2007.

Casi, Giulio et al. "Antibody drug conjugates: Basic concepts, examples and future perspectives." Journal of Controlled Release, vol. 161, No. 2, Jan. 10, 2012.

Cocco, E. et al. "hI-con1, a factor for VII-IgGFc chimeric protein targeting tissue factor for immunotherapy of uterine serous papillary carcinoma." Br. J. Cancer, 2010, vol. 3, is. 6. pp. 812-819, the abstract, pp. 813-818.

Giulio, Casi et al. "Antibody-drug conjugates: Basic concepts, examples and future perspectives." Journal of Controlled Release, 2012, vol. 161, No. 2, pp. 422-428.

Kalwy, S. et al. "Toward more efficient protein expression." Molecular Biotechnology, Humana Press, Inc., vol. 34, No. 2, Sp. Iss. SI, Oct. 1, 2006.

Kotsopoulou, E. et al. "Optimised mammalian expression through the coupling of codon adaptation with gene amplification; maximum yields with minimum effort." Journal of Biotechnology, vol. 146, No. 4, Apr. 15, 2010.

Liu, H. et al. "Heterogenecity of monoclonal antibodies." Pharmaceutical Sciences, American Pharmaceutical Assoc., 2007, vol. 97, No. 7, pp. 2426-2447.

Ortiz-Sanchez, Elizabeth et al. "Antibody cytokine fusion proteins: applications in cancer therapy." Expert Opinion on Biological Therapy, vol. 8, No. 5, May 1, 2008.

Qian, Yueming et al. "Cell Culture and Gene Transcription Effects of Copper Sulfate on Chinese Hamster Ovary Cells." Biotechnology Progress, 2011, vol. 27, No. 4, pp. 1190-1194.

Anti-EGFR1-TGFβRII fusion protein at LC constant region

Amino acid sequence of Anti-EGFR1 heavy chain:

QVQLKQSGPGLVQPSQSLSITCTVSGFSLTNYGVHWVRQSPG
KGLEWLGVIWSGGNTDYNTPFTSRLSINKDNSKSQVFFKMNSL
QSNDTAIYYCARALTYYDYEFAYWGQGTLVTVSAASTKGPSVF
PLAPSSKSTSGGTAALGCLVKDYFPEPVTVSWNSGALTSGVHT
FPAVLQSSGLYSLSSVVTVPSSSLGTQTYICNVNHKPSNTKVDK
RVEPKSCDKTHTCPPCPAPELLGGPSVFLFPPKPKDTLMISRTP
EVTCVVVDVSHEDPEVKFNWYVDGVEVHNAKTKPREEQYNST
YRVVSVLTVLHQDWLNGKEYKCKVSNKALPAPIEKTISKAKGQP
REPQVYTLPPSRDELTKNQVSLTCLVKGFYPSDIAVEWESNGQ
PENNYKTTPPVLDSDGSFFLYSKLTVDKSRWQQGNVFSCSVM
HEALHNHYTQKSLSLSPG

Amino acid sequence of Anti-EGFR1 light chain fusion protein:

DILLTQSPVILSVSPGERVSFSCRASQSIGTNIHWYQQRTNGSP
RLLIKYASESISGIPSRFSGSGSGTDFTLSINSVESEDIADYYCQQ
NNNWPTTFGAGTKLELKRTVAAPSVFIFPPSDEQLKSGTASVVC
LLNNFYPREAKVQWKVDNALQSGNSQESVTEQDSKDSTYSLS
STLTLSKADYEKHKVYACEVTHQGLSSPVTKSFNRGEC*GGGGS
GGGGSGGGGS*TIPPHVQKSVNNDMIVTDNNGAVKFPQLCKFC
DVRFSTCDNQKSCMSNCSITSICEKPQEVCVAVWRKNDENITL
ETVCHDPKLPYHDFILEDAASPKCIMKEKKKPGETFFMCSCSS
DECNDNIIFSEEYNTSNPD

Figure 1

SEQ ID NO: 5
Codon optimized Anti-EGFR1 Heavy chain sequence:
```
   1 CAGGTGCAGC TGAAGCAGTC TGGCCCTGGC CTGGTGCAGC CTCCCAGTC CCTGTCCATC
  61 ACCTGTACCG TGTCCGGCTT CTCCCTGACC AACTACGGCG TGCACTGGGT GCGACAGTCC
 121 CCCGGCAAGG GCCTGGAATG GCTGGGAGTG ATTTGGAGCG GCGGCAACAC CGACTACAAC
 181 ACCCCCTTCA CCTCCCGGCT GTCCATCAAC AAGGACAACT CCAAGTCCCA GGTGTTCTTC
 241 AAGATGAACT CCCTGCAGTC CAACGACACC GCCATCTACT ACTGCGCCAG AGCCCTGACC
 301 TACTATGACT ACGAGTTCGC CTACTGGGGC CAGGGCACCC TGGTGACAGT GTCCGCCGCT
 361 TCCACCAAGG GCCCCTCCGT GTTCCCTCTG GCCCCCTCCA GCAAGTCCAC CTCTGGCGGC
 421 ACCGCTGCCC TGGGCTGCCT GGTGAAAGAC TACTTCCCCG AGCCCGTGAC CGTGTCCTGG
 481 AACTCTGGCG CCCTGACCTC CGGCGTGCAC ACCTTCCCTG CCGTGCTGCA GTCCTCCGGC
 541 CTGTACTCCC TGTCCTCCGT GGTGACCGTG CCCTCCAGCT CTCTGGGCAC CCAGACCTAC
 601 ATCTGCAACG TGAACCACAA GCCCTCCAAC ACCAAGGTGG ACAAGCGGGT GGAACCCAAG
 661 TCCTGCGACA AGACCCACAC CTGTCCCCCC TGCCCTGCCC CTGAACTGCT GGGCGGACCT
 721 TCCGTGTTCC TGTTCCCCCC AAAGCCCAAG GACACCCTGA TGATCTCCCG GACCCCCGAA
 781 GTGACCTGCG TGGTGGTGGA CGTGTCCCAC GAGGACCCTG AAGTGAAGTT CAATTGGTAC
 841 GTGGACGGCG TGGAAGTGCA CAACGCCAAG ACCAAGCCCA GAGAGGAACA GTACAACTCC
 901 ACCTACCGGG TGGTGTCTGT GCTGACCGTG CTGCACCAGG ACTGGCTGAA CGGCAAAGAG
 961 TACAAGTGCA AGGTGTCCAA CAAGGCCCTG CCTGCCCCCA TCGAAAAGAC CATCTCCAAG
1021 GCCAAGGGCC AGCCCCGCGA GCCCCAGGTG TACACCCTGC CCCCTAGCCG GGACGAGCTG
1081 ACCAAGAACC AGGTGTCCCT GACCTGTCTG GTGAAAGGCT TCTACCCCTC CGATATCGCC
1141 GTGGAATGGG AGTCCAACGG CCAGCCCGAG AACAACTACA AGACCACCCC CCCTGTGCTG
1201 GACTCCGACG GCTCATTCTT CCTGTACTCC AAGCTGACCG TGGACAAGTC CCGGTGGCAG
1261 CAGGGCAACG TGTTCTCCTG CTCCGTGATG CACGAGGCCC TGCACAACCA CTACACCCAG
1321 AAGTCCCTGT CTCTGTCCCC CGGC
```

SEQ ID NO: 6
Codon optimized Anti-EGFR1 light chain nucleotide sequence:
```
   1 GACATCCTGC TGACCCAGTC CCCCGTGATC CTGTCCGTGT CTCCTGGCGA GCGGGTGTCC
  61 TTCTCCTGCC GGGCCTCTCA GTCCATCGGC ACCAACATCC ACTGGTATCA GCAGCGGACC
 121 AACGGCTCCC CTCGGCTGCT GATTAAGTAC GCCTCCGAGT CCATCTCCGG CATCCCTTCC
 181 CGGTTCTCCG GCTCCGGCTC TGGCACCGAC TTCACCCTGT CCATCAACTC CGTGGAATCC
 241 GAGGACATTG CCGACTACTA CTGCCAGCAG AACAACAACT GGCCCACCAC CTTCGGCGCT
 301 GGCACCAAGC TGGAACTGAA AGCGGACGTG GCCGCTCCCT CCGTGTTCAT CTTCCCACCC
 361 TCCGACGAGC AGCTGAAGTC CGGCACCGCC TCCGTGGTGT GCCTGCTGAA CAACTTCTAC
 421 CCCCGCGAGG CCAAGGTGCA GTGGAAGGTG GACAACGCCC TGCAGTCCGG CAACTCCCAG
 481 GAATCCGTGA CCGAGCAGGA CTCCAAGGAC AGCACCTACT CCCTGTCCTC CACCCTGACC
 541 CTGTCCAAGG CCGACTACGA GAAGCACAAG GTGTACGCCT GCGAAGTGAC CCACCAGGGC
 601 CTGTCCAGCC CCGTGACCAA GTCCTTCAAC CGGGGCGAGT GTGG
```

SEQ ID NO: 7
Codon optimized nucleotide sequence of TGFβRII:
```
   1 ACAATCCCTC CACACGTGCA GAAATCCGTG AACAACGACA TGATCGTGAC CGACAACAAT
  61 GGCGCCGTGA AGTTCCCCCA GCTGTGCAAG TTCTGCGACG TGCGGTTCTC TACCTGCGAC
 121 AACCAGAAAT CCTGCATGTC CAACTGCTCC ATCACCTCCA TCTGCGAGAA GCCCCAGGAA
 181 GTGTGCGTGG CCGTGTGGCG GAAGAACGAC GAGAACATCA CCCTGGAAAC CGTGTGCCAC
 241 GACCCCAAGC TGCCCTACCA CGACTTCATC CTGGAAGATG CCGCCTCCCC CAAGTGCATC
 301 ATGAAGGAAA AGAAGAAGCC CGGCGAGACT TTCTTCATGT GCAGCTGCTC CTCCGACGAG
 361 TGCAACGACA ACATCATCTT CTCCGAAGAG TACAACACCT CCAACCCCGA C
```

SEQ ID NO: 8
Codon optimized nucleotide sequence of the Linker:
```
   1 GGAGGCGGAG GATCTGGCGG AGGTGGAAGT GGCGGCGGAG GCTCT
```

Figure 2

Anti-EGFR1-TGFβRII (LC-C-terminus):

Amino acid sequence of Anti-EGFR1 heavy chain: SEQ ID NO: 1

QVQLKQSGPGLVQPSQSLSITCTVSGFSLTNYGVHWVRQSPGKGLEWLGVIWSGGNTDYNTPFT
SRLSINKDNSKSQVFFKMNSLQSNDTAIYYCARALTYYDYEFAYWGQGTLVTVSAASTKGPSVF
PLAPSSKSTSGGTAALGCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSPG

Amino acid sequence of Anti-EGFR1 LC constant-TGFβRII fusion protein: SEQ ID NO: 9

DILLTQSPVILSVSPGERVSFSCRASQSIGTNIHWYQQRTNGSPRLLIKYASESISGIPSRFSG
SGSGTDFTLSINSVESEDIADYYCQQNNNWPTTFGAGTKLELKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGECGGGGSGGGGSGGGGSTIPPHVQKSVNNDMIVTDNNGAVKFPQ
LCKFCDVRFSTCDNQKSCMSNCSITSICEKPQEVCVAVWRKNDENITLETVCHDFKLPYHDFIL
EDAASPKCIMKEKKKPGETFFMCSCSSDECNDNIIFSEEYNTSNPD

Figure 3

SEQUENCE LISTING

<160> NUMBER OF SEQ ID NOS: 11

<210> SEQ ID NO 1
<211> LENGTH: 448
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr

```
               355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Synthetic Construct

<400> SEQUENCE: 2

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 3
<211> LENGTH: 137
<212> TYPE: PRT
<213> ORGANISM: Artificial Sequence
<220> FEATURE:
<223> OTHER INFORMATION: Synthetic Construct

<400> SEQUENCE: 3
```

```
Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 1344
<212> TYPE: DNA
<213> ORGANISM: Artificial Sequence
<220> FEATURE:
<223> OTHER INFORMATION: Synthetic Construct

<400> SEQUENCE: 5
caggtgcagc tgaagcagtc tggccctggc ctggtgcagc cctcccagtc cctgtccatc      60
acctgtaccg tgtccggctt ctccctgacc aactacggcg tgcactgggt gcgacagtcc     120
cccggcaagg gcctggaatg gctgggagtg atttggagcg gcggcaacac cgactacaac     180 accccccttca cctcccggct gtccatcaac aaggacaact ccaagtccca ggtgttcttc     240
aagatgaact ccctgcagtc caacgacacc gccatctact actgcgccag agccctgacc     300
tactatgact acgagttcgc ctactggggc cagggcaccc tggtgacagt gtccgccgct     360
tccaccaagg gccctccgt gttccctctg gcccctcca gcaagtccac ctctggcggc     420
accgctgccc tgggctgcct ggtgaaagac tacttcccg agcccgtgac cgtgtcctgg     480
aactctggcg ccctgaccct cggcgtgcac accttcctg ccgtgctgca gtcctccggc     540
ctgtactccc tgtcctccgt ggtgaccgtg ccctccagct ctctgggcac ccagacctac     600
atctgcaacg tgaaccacaa gcctccaac accaaggtgg acaagcgggt ggaaccaag     660 tcctgcgaca gacccacac ctgtcccccc tgccctgccc ctgaactgct gggcggacct     720
tccgtgttcc tgttccccc aaagcccaag gacaccctga tgatctcccg gacccccgaa     780
gtgacctgcg tggtggtgga cgtgtcccac gaggaccctg aagtgaagtt caattggtac     840
gtggacggcg tggaagtgca caacgccaag accaagccca gagaggaaca gtacaactcc     900
```

```
acctaccggg tggtgtctgt gctgaccgtg ctgcaccagg actggctgaa cggcaaagag      960
tacaagtgca aggtgtccaa caaggccctg cctgccccca tcgaaaagac catctccaag     1020
gccaagggcc agccccgcga gccccaggtg tacaccctgc ccctagccg ggacgagctg      1080 accaagaacc aggtgtccct gacctgtctg gtgaaaggct ctaccccctc cgatatcgcc     1140
gtggaatggg agtccaacgg ccagcccgag aacaactaca agaccacccc ccctgtgctg     1200
gactccgacg gctcattctt cctgtactcc aagctgaccg tggacaagtc cggtggcag      1260 cagggcaacg tgttctcctg ctccgtgatg cacgaggccc tgcacaacca ctacacccag     1320
aagtccctgt ctctgtcccc cggc                                            1344
```

<210> SEQ ID NO 6
<211> LENGTH: 642
<212> TYPE: DNA
<213> ORGANISM: Artificial Sequence
<220> FEATURE:
<223> OTHER INFORMATION: Synthetic Construct

<400> SEQUENCE: 6

```
gacatcctgc tgacccagtc ccccgtgatc ctgtccgtgt ctcctggcga gcgggtgtcc       60
ttctcctgcc gggcctctca gtccatcggc accaacatcc actggtatca gcagcggacc      120
aacggctccc ctcggctgct gattaagtac gcctccgagt ccatctccgg catcccttcc      180
cggttctccg gctccggctc tggcaccgac ttcaccctgt ccatcaactc cgtggaatcc      240
gaggacattg ccgactacta ctgccagcag aacaacaact ggcccaccac cttcggcgct      300
ggcaccaagc tggaactgaa gcggaccgtg gccgctccct ccgtgttcat cttcccaccc      360
tccgacgagc agctgaagtc cggcaccgcc tccgtggtgt gcctgctgaa caacttctac      420
ccccgcgagg ccaaggtgca gtggaaggtg gacaacgccc tgcagtccgg caactcccag      480
gaatccgtga ccgagcagga ctccaaggac agcacctact cccctgtcctc caccctgacc      540 ctgtccaagg ccgactacga aagcacaag gtgtacgcct gcgaagtgac ccaccagggc      600
ctgtccagcc ccgtgaccaa gtccttcaac cggggcgagt gt                         642
```

<210> SEQ ID NO 7
<211> LENGTH: 411
<212> TYPE: DNA
<213> ORGANISM: Artificial Sequence
<220> FEATURE:
<223> OTHER INFORMATION: Synthetic Construct

<400> SEQUENCE: 7

```
acaatccctc cacacgtgca gaaatccgtg aacaacgaca tgatcgtgac cgacaacaat       60
ggcgccgtga gttcccccca gctgtgcaag ttctgcgacg tgcggttctc tacctgcgac      120
aaccagaaat cctgcatgtc caactgctcc atcacctcca tctgcgagaa gccccaggaa      180
gtgtgcgtgg ccgtgtggcg gaagaacgac gagaacatca ccctggaaac cgtgtgccac      240
gaccccaagc tgcccctacca cgacttcatc ctggaagatg ccgcctcccc caagtgcatc      300
atgaaggaaa agaagaagcc cggcgagact ttcttcatgt gcagctgctc ctccgacgag      360
tgcaacgaca acatcatctt ctccgaagag tacaacacct ccaaccccga c              411
```

<210> SEQ ID NO 8
<211> LENGTH: 45
<212> TYPE: DNA
<213> ORGANISM: Artificial Sequence
<220> FEATURE:

<223> OTHER INFORMATION: Synthetic Construct

<400> SEQUENCE: 8
ggaggcggag gatctggcgg aggtggaagt ggcggcggag gctct        45

<210> SEQ ID NO 9
<211> LENGTH: 366
<212> TYPE: PRT
<213> ORGANISM: Artificial Sequence
<220> FEATURE:
<223> OTHER INFORMATION: Synthetic Construct

<400> SEQUENCE: 9

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Thr Ile Pro Pro His Val Gln Lys Ser Val Asn
225                 230                 235                 240

Asn Asp Met Ile Val Thr Asp Asn Asn Gly Ala Val Lys Phe Pro Gln
                245                 250                 255

Leu Cys Lys Phe Cys Asp Val Arg Phe Ser Thr Cys Asp Asn Gln Lys
            260                 265                 270

Ser Cys Met Ser Asn Cys Ser Ile Thr Ser Ile Cys Glu Lys Pro Gln
        275                 280                 285

Glu Val Cys Val Ala Val Trp Arg Lys Asn Asp Glu Asn Ile Thr Leu
    290                 295                 300

Glu Thr Val Cys His Asp Pro Lys Leu Pro Tyr His Asp Phe Ile Leu
305                 310                 315                 320

Glu Asp Ala Ala Ser Pro Lys Cys Ile Met Lys Glu Lys Lys Pro
                325                 330                 335
```

```
Gly Glu Thr Phe Phe Met Cys Ser Cys Ser Ser Asp Glu Cys Asn Asp
                340                 345                 350

Asn Ile Ile Phe Ser Glu Glu Tyr Asn Thr Ser Asn Pro Asp
        355                 360                 365
```

<210> SEQ ID NO 10
<211> LENGTH: 448
<212> TYPE: PRT
<213> ORGANISM: Artificial Sequence
<220> FEATURE:
<223> OTHER INFORMATION: Synthetic Construct

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 11
<211> LENGTH: 214
<212> TYPE: PRT
<213> ORGANISM: Artificial Sequence
<220> FEATURE:
<223> OTHER INFORMATION: Synthetic Construct

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210
```

IMMUNOTHERAPY METHODS USING ANTI-PD-L1 ANTIBODIES IN COMBINATION WITH EGFR1 TARGETED-TGF-BETA IMMUNOMODULATORY FUSION PROTEINS

CROSS REFERENCE TO RELATED APPLICATIONS

The application is a Continuation-in-Part application and claims priority to copending U.S. patent application Ser. No. 15/795,404 filed on Oct. 27, 2017, which in turn claims priority to U.S. patent application Ser. No. 15/047,062 filed on Feb. 18, 2016, now U.S. Pat. No. 9,809,651 issued on Nov. 7, 2017, which in turn claims priority to U.S. patent application Ser. No. 14/458,674 filed on Aug. 13, 2014, now U.S. Pat. No. 9,340,617 which in turn claims priority to U.S. patent application No. 13/799,409 filed on Mar. 13, 2013, now U.S. Pat. No. 8,815,247, which in turn claims priority to Indian Patent Application No. 1689/CHE/2012 filed on Apr. 30, 2012 and Indian Patent Application No. 1690/CHE/2012 filed on Apr. 30, 2012, the contents of all are hereby incorporated by reference herein for all purposes.

BACKGROUND OF THE INVENTION

Technical Field

The present invention provides for a composition and a method for treating a subject afflicted with a cancer, wherein the composition comprises therapeutically effective amounts of: (a) an anti-Programmed Death-Ligand 1 (PD-L1) antibody and (b) a targeted/immunomodulatory fusion protein comprising at least one tumor targeting moiety and at least one immunomodulatory moiety that counteracts the immune tolerance of cancer cells.

Related Art

The immune system provides the human body with a means to recognize and defend itself against microorganisms and substances recognized as foreign or potentially harmful. While passive immunotherapy of cancer with monoclonal antibodies and passive transfer of T cells to attack tumor cells have demonstrated clinical efficacy, the goal of active therapeutic vaccination to induce these immune effectors and establish immunological memory against tumor cells has remained challenging. Several tumor-specific and tumor-associated antigens have been identified, yet these antigens are generally weakly immunogenic and tumors employ diverse mechanisms to create a tolerogenic environment that allows them to evade immunologic attack.

Significant research has therefore been devoted to immune therapies, including the field of immuno-oncology, which is now recognized as a strategy for treating cancer. In recent years, new targets and compounds that manipulate the immune response have been studied by researchers and clinicians. For example, agents that target programmed cell death protein 1 (PD-1) and programmed death-ligand 1 (PD-L1) have been developed and approved.

Nonetheless, even these new immunotherapies are only effective in certain patients. Indeed, despite the attention to such new agents, responses and prolonged survival in many patients is still quite poor. Therefore, in light of the variability in response to both long-established therapies and new immunotherapies, and the desire to maximize clinical benefit, there remains a need for improved treatment options, including more effective combinations with immune therapeutic agents.

SUMMARY OF THE INVENTION

The present invention provides for expressed targeted/immunomodulatory fusion polypeptides in combination with an antibody useful in the treatment of cancer that binds to an inhibitory immune checkpoint, such as PD-L1. The present invention further provides methods of reducing growth of cancer cells by counteracting immune tolerance of cancer cells, wherein T cells remain active and inhibit the recruitment of T-regulatory that are known to suppress the immune system's response to the tumor.

In one aspect, the present invention provides for a combination of cancer therapeutic agents comprising an anti-PD-L1 antibody and a chimeric targeted/immunomodulatory fusion polypeptide comprising at least one tumor targeting moiety to target a cancer cell and at least one immunomodulating moiety that counteracts immune tolerance of cancer cell. The tumor targeting moiety and the immunomodulating moiety are preferably linked by an amino acid spacer of sufficient length of amino acid residues so that both moieties can successfully bond to their individual target. In the alternative, the tumor targeting moiety and the immunomodulating moiety that counteract immune tolerance of cancer cell may be bound directly to each other. The chimeric targeted/immunomodulatory fusion polypeptides of the invention are useful for binding to a cancer cell receptor and reducing the ability of cancer cells to avoid an immune response.

In another aspect, the present invention provides a targeted/immunomodulatory fusion polypeptide including at least one tumor targeting moiety fused with at least one immunomodulatory moiety. The immunomodulatory moiety specifically binds to Transforming growth factor-beta (TGF-β) and the tumor targeting moiety includes an antibody, antibody fragment including the light or heavy chains of the antibody, scFv, or Fc-containing polypeptide that specifically binds a component of a tumor cell, tumor antigen, tumor vasculature, tumor microenvironment, or tumor-infiltrating immune cell.

In a still further aspect, the combination comprises an anti-PD-L1 antibody and a chimeric targeted/immunomodulatory fusion polypeptide that comprised a tumor targeting moiety and an immunomodulatory moiety comprising a molecule that binds transforming growth factor beta (TGF-β), wherein the tumor targeting moiety is an antibody that binds to EGFR1, where in the antibody can be the full antibody, heavy chain or light chain.

In one aspect, the immunomodulating moiety may be linked to the tumor targeting moiety by an amino acid spacer of sufficient length to allow bi-specific binding of the molecule. The immunomodulating moiety may be bound to either the C-terminus of the heavy or light chain of the tumor targeting antibody.

In yet another aspect, the immunomodulatory moiety includes a molecule that binds TGF-β and inhibits the function thereof. Specifically, the immunomodulatory moiety includes an extracellular ligand-binding domain of Transforming growth factor-beta receptor TGF-βRII, TGF-βRIIb, or TGF-βRIII. In another aspect the immunomodulatory moiety includes an extracellular ligand-binding domain (ECD) of TGF-βRII.

In a further aspect, the invention provides for a method for immunotherapy of a subject afflicted with cancer, which method comprises administering to the subject a composition comprising a therapeutically effective amount of an anti-PD-L1 antibody and a chimeric targeted/immunomodulatory fusion polypeptide comprising an immunomodulatory moiety comprising a molecule that binds transforming growth factor beta (TGF-β), wherein the tumor targeting moiety is an antibody that binds to EGFR1.

In another aspect, are described methods, wherein the cancer is characterized by overexpression of PD-L1 and/or EGFR1.

In a still further aspect, the present invention provides for a method for treating cancer comprising an anti-PD-L1 antibody and a chimeric targeted/immunomodulatory fusion polypeptide of the present invention wherein the components are administered sequentially in either order or simultaneously. The components can be administered sequentially in either order or simultaneously, during a treatment cycle of 7 days to several months. Further, the components may be administered either in a single composition, or as two distinct compositions using different administration routes, including intravenous infusion, oral or other known methods of delivery.

In a further aspect, the present invention provides for a kit for treating cancer comprising a combination of an anti-PD-L1 antibody and a chimeric polypeptide comprising an immunomodulatory moiety that binds to and traps transforming growth factor beta (TGF-β) and a tumor targeting moiety that is an antibody that binds to EGFR1.

In yet another aspect, the present invention provides a method of treating a cancer in a patient in need thereof, wherein the method comprises, administering to the patient a combination consisting essentially of an anti-PD-L1 antibody and a chimeric targeted/immunomodulatory fusion polypeptide comprising an immunomodulatory moiety and a tumor targeting molecule wherein the immunomodulatory moiety binds to transforming growth factor beta (TGF-β), and wherein the tumor targeting moiety is an antibody that binds to EGFR1.

In one aspect, the present invention provides for optimized genes encoding for a chimeric targeted/immunomodulatory fusion polypeptide comprising at least one tumor targeting moiety and at least one immunomodulatory moiety for treating cancer in a human subject wherein the optimized genes have been modified to increase expression in a human subject. Preferably the optimized genes comprise sequences for encoding a tumor targeting moiety or an immunomodulatory moiety selected from SEQ ID NOs: 5 to 8.

In another aspect, the present invention provides for a vector comprising optimized genes for CG sequences for expression of the chimeric targeted/immunomodulatory fusion polypeptide. Preferably, the vector includes sequences for encoding at least one tumor targeting moiety and at least one immunomodulatory moiety include SEQ ID NOs: 5 to 8.

In yet a further aspect, the present invention relates to the use of a chimeric targeted/immunomodulatory fusion protein, as shown in FIGS. 1 and 3 in combination with an anti-PD-L1 antibody, in the use of a medicament for the treatment of cancer. Preferably, the targeted/immunomodulatory fusion protein is expressed in a host cell and such expressed proteins are administered in a therapeutic amount in combination with a anti PD-L1 antibody to reduce the effects of cancer in a subject in need thereof.

In a still further aspect, the present invention provides for a method for increasing IFNγ release and TGF-β1 trapping in cancer cells, the method comprising introducing to the cancer cells a combination of a therapeutically effective amount of an anti-PD-L1 antibody and a chimeric targeted/immunomodulatory fusion polypeptide comprising an immunomodulatory moiety that binds to transforming growth factor beta (TGF-β) and a tumor targeting moiety that binds to EGFR1.

The method of the present invention provides nucleotide sequences that encode the therapeutically active targeted/immunomodulatory fusion proteins of the present invention and such expression may be conducted in a transient cell line or a stable cell line. The transient expression is accomplished by transfecting or transforming the host with vectors carrying the fusion proteins into mammalian host cells. Once the targeted/immunomodulatory fusion proteins are expressed, they are preferably subjected to purification and in-vitro tests to check its bi-specificity, that being, having the ability to bind to both the tumor target moiety and immunomodulating moiety. Such tests may include in-vitro test such as ELISA or NK/T-cell binding assays to validate bi-functional target binding or immune cell stimulation.

Notably once the specific targeted/immunomodulatory fusion proteins demonstrate the desired bi-specificity, such targeted/immunomodulatory fusion proteins are selected for sub-cloning into a stable cell line for larger scale expression and purification. Such stable cell lines are previously disclosed, such as a mammalian cell line, including but not limited to HEK293, CHO or NSO.

In a further aspect, the culture medium can be improved by additions to such medium. For example, the culture medium may include a divalent transitional metallic salt which is added to the cell culture either initially or in fed-batch mode to reduce accumulation of lactate during culturing and/or reduce heterogeneity of the fusion proteins. A desirable transitional metallic salt includes a zinc ion and the addition of the metal ion may be carried out during different phases of the production.

Other features and advantages of the invention will be apparent from the following detailed description, drawings and claims.

BRIEF DESCRIPTION OF THE DRAWINGS

FIG. 1 shows the amino acid sequences of Anti-EGFR1-TGFβRII fusion protein at LC constant region with amino acid sequence of Anti-EGFR1 heavy chain (SEQ ID NO: 1) and the amino acid sequence of Anti-EGFR1 light chain (SEQ ID NO: 2) attached to amino acid residues for TGF-βRII (immunomodulatory moiety) (SEQ ID NO: 3) identified in bold letters and wherein a linker (SEQ ID NO: 4) is positioned between the Anti-EGFR1 light chain and TGF-βRII and shown in italics.

FIG. 2 shows the optimized codon nucleotide sequences used for expression of the targeted/immunomodulatory fusion proteins of the present invention, including Anti-EGFR1 heavy chain (SEQ ID NO: 5); Anti-EGFR1 light chain (SEQ ID NO: 6); Linker (SEQ ID NO: 8); and TGFβRII (SEQ ID NO: 7) that have been codon optimized for expression in CHO cell.

FIG. 3 shows the amino acid sequences for Anti-EGFR1 HC+Anti-EGFR1 LC-TGFβRII (FmAb2) wherein the TGFβRII molecule is connected to the C terminus of the light chain separated by a linker and including SEQ ID NOs: 1 and 9.

DETAILED DESCRIPTION OF THE INVENTION

Figure 4:
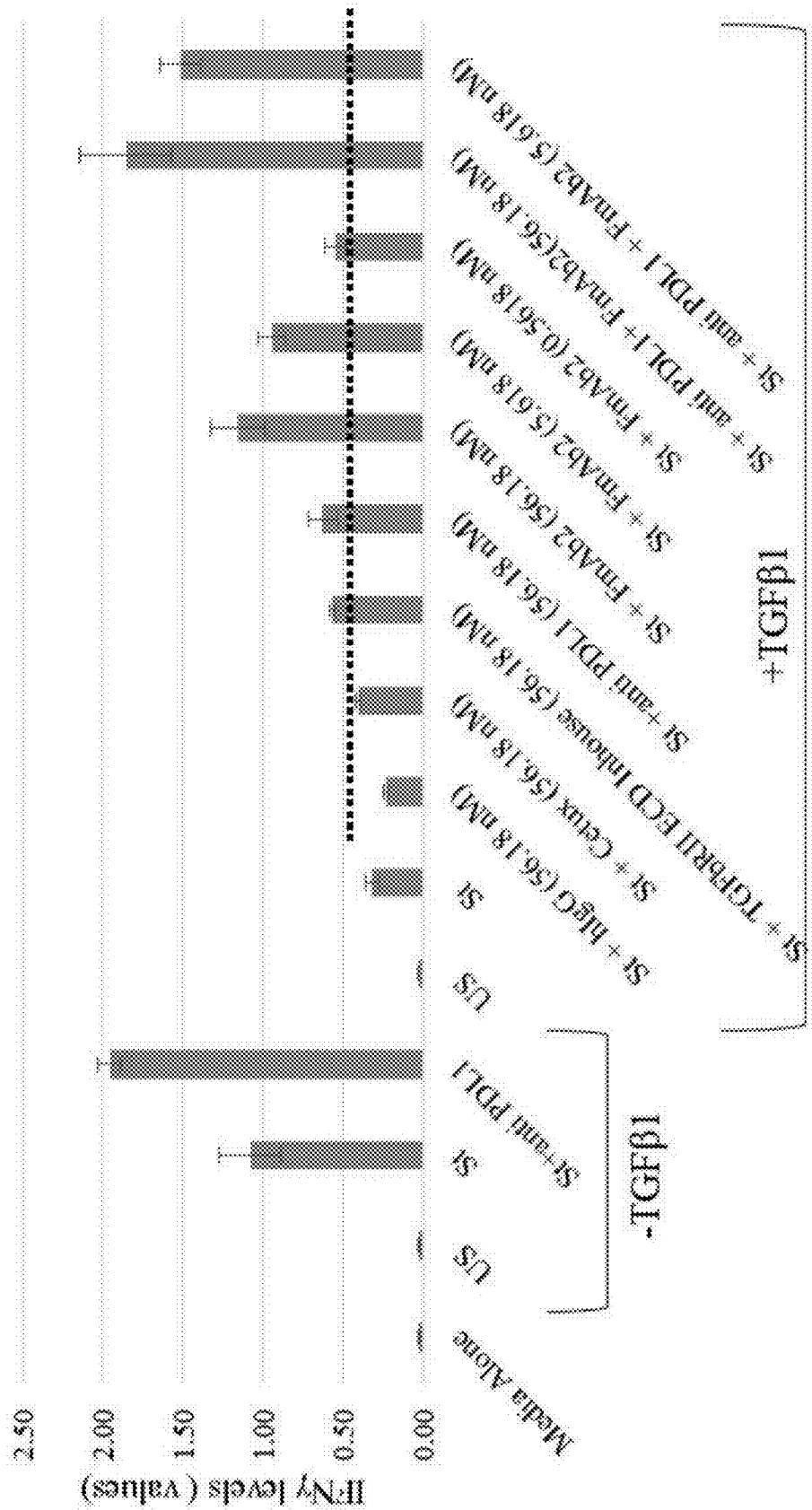
FIG. 4 shows a graph indicating IFNγ release by stimulated Human PBMCs (anti CD3 added at 2 ng/mL) in the presence of FmAb2 antibody added at a titrating concentration. The graph also includes the data from combination of FmAb2 with anti PD-L1 antibody.

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

Unless otherwise defined, all technical and scientific terms used herein have the meaning commonly understood by one of ordinary skill in the art to which this invention belongs. The terminology used herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. The following terms have the meanings given:

The term "polynucleotide" as used herein means a sequence of nucleotides connected by phosphodiester linkages. Polynucleotides are presented herein in the direction from the 5' to the 3' direction. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U). A polynucleotide of the present invention can be prepared using standard techniques well known to one of skill in the art.

The term "optimized" as used herein means that a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in CHO mammalian cells; however optimized expression of these sequences in other eukaryotic cells is also envisioned herein.

The amino acid sequences encoded by optimized nucleotide sequences are also referred to as optimized.

The term "expression" as used herein is defined as the transcription and/or translation of a particular nucleotide sequence driven by its promoter.

The term "transfection" of a cell as used herein means that genetic material is introduced into a cell for the purpose of genetically modifying the cell. Transfection can be accomplished by a variety of means known in the art, such as transduction or electroporation.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, ocular cancer, pancreatic cancer, colorectal cancer, renal cancer, liver cancer, brain cancer, lymphoma, leukemia, lung cancer and the like.

The term "transgene" is used in a broad sense to mean any heterologous nucleotide sequence incorporated in a vector for expression in a target cell and associated expression control sequences, such as promoters. It is appreciated by those of skill in the art that expression control sequences will be selected based on ability to promote expression of the transgene in the target cell. An example of a transgene is a nucleic acid encoding a chimeric targeted/immunomodulatory fusion protein of the present invention.

The term "expression vector" as used herein means a vector containing a nucleic acid sequence coding for at least a part of a gene product capable of being transcribed. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well. The term also includes a recombinant plasmid or virus that comprises a polynucleotide to be delivered into a host cell, either in vitro or in vivo. Preferably the host cell is a transient cell line or a stable cell line and more preferably a mammalian host cell and selected from the group consisting of HEK293, CHO and NSO.

The term "subject," as used herein means a human or vertebrate animal including a dog, cat, horse, cow, pig, sheep, goat, chicken, monkey, rat, and mouse.

The term "fusion protein" and a "fusion polypeptide" as used herein means a polypeptide having two portions covalently linked together, where each of the portions is a polypeptide having a different property. The property may be a biological property, such as activity in vitro or in vivo. The property may also be simple chemical or physical property, such as binding to a target molecule, catalysis of a reaction, etc. The two portions may be linked directly by a single peptide bond or through a peptide linker.

The term "therapeutically effective amount" as used herein means the amount of the subject compound that will elicit the biological or medical response of a tissue, system, animal or human that is being sought by the researcher, veterinarian, medical doctor or other clinician.

The term "pharmaceutically acceptable" as used herein means the carrier, diluent or excipient must be compatible with the other ingredients of the formulation and not deleterious to the recipient thereof.

The term "recombinant" as used herein means a genetic entity distinct from that generally found in nature. As applied to a polynucleotide or gene, this means that the polynucleotide is the product of various combinations of cloning, restriction and/or ligation steps, and other procedures that result in the production of a construct that is distinct from a polynucleotide found in nature.

The term "substantial identity" or "substantial similarity," as used herein when referring to a nucleic acid or fragment thereof, indicates that when optimally aligned with appropriate nucleotide insertions or deletions with another nucleic acid (or its complementary strand), there is nucleotide sequence identity in at least about 95 to 99% of the sequence.

The term "peptide," "polypeptide" and "protein" are used interchangeably to denote a sequence polymer of at least two amino acids covalently linked by an amide bond.

The term "homologous" as used herein and relating to peptides refers to amino acid sequence similarity between two peptides. When an amino acid position in both of the peptides is occupied by identical amino acids, they are homologous at that position. Thus by "substantially homologous" means an amino acid sequence that is largely, but not entirely, homologous, and which retains most or all of the activity as the sequence to which it is homologous. As used herein, "substantially homologous" as used herein means that a sequence is at least 50% identical, and preferably at least 75% and more preferably 95% homology to the reference peptide. Additional peptide sequence modifications are included, such as minor variations, deletions, substitutions or derivitizations of the amino acid sequence of the sequences disclosed herein, so long as the peptide has substantially the same activity or function as the unmodified peptides. Notably, a modified peptide will retain activity or function associated with the unmodified peptide, the modified peptide will generally have an amino acid sequence "substantially homologous" with the amino acid sequence of the unmodified sequence.

The term "administering" as used herein is defined as the actual physical introduction of the composition into or onto (as appropriate) the host subject. Any and all methods of introducing the composition into the subject are contemplated according to the present invention; the method is not dependent on any particular means of introduction and is not to be so construed. Means of introduction are well-known to those skilled in the art, and preferably, the composition is administered subcutaneously or intratumorally. One skilled in the art will recognize that, although more than one route can be used for administration, a particular route can provide a more immediate and more effective reaction than another route. Local or systemic delivery can be accomplished by administration comprising application or instillation of the immunovaccines into body cavities, inhalation or insufflation of an aerosol, or by parenteral introduction, comprising intramuscular, intravenous, intraportal, intrahepatic, peritoneal, subcutaneous, or intradermal administration. In the event that the tumor is in the central nervous system, the composition must be administered intratumorally because there is no priming of the immune system in the central nervous system.

The present invention provides strategies to counteract tumor-induced immune tolerance in the tumor microenvironment and can enhance the antitumor efficacy of chemotherapy by activating and leveraging T cell-mediated adaptive antitumor immunity against disseminated cancer cells.

The present invention is based on the discovery that the targeted/immunomodulatory fusion proteins of the present invention in combination with an anti-PD-L1 antibody can increase levels of IFNγ to counteract or reverse immune tolerance of cancer cells. It is known that cancer cells are able to escape elimination by chemotherapeutic agents or tumor-targeted antibodies via specific immunosuppressive mechanisms in the tumor microenvironment and such ability of cancer cells is recognized as immune tolerance. By counteracting tumor-induced immune tolerance, the present invention provides effective compositions and methods for cancer treatment by using a combination of an anti-PD-L1 antibody and the chimeric targeted/immunomodulatory fusion polypeptide of the present invention.

The increased expression of immunosuppressive cytokines (TGF-β1; PD-L1) and tumor-infiltrating Tregs is correlated with a reduction of survival of patients with diverse types of cancers. The targeted/immunomodulatory fusion protein of the present invention in combination with an anti-PD-L1 antibody inhibit key immunosuppressive molecules expressed by the targeted tumor cell or tumor-infiltrating Treg cells and myeloid suppressor cells (DCs or MDSC). As such, they provide the targeted ability to inhibit the development or function of Tregs within the tumor microenvironment.

As used herein, the term "antibody" includes natural or artificial mono- or polyvalent antibodies including, but not limited to, polyclonal, monoclonal, multispecific, human, humanized or chimeric antibodies, single chain antibodies, Fab fragments. F(ab') fragments, fragments produced by a Fab expression library, anti-idiotypic (anti-Id) antibodies (including, e.g., anti-Id antibodies to antibodies of the invention), and epitope-binding fragments of any of the above. The antibody may be from any animal origin including birds and mammals. In one aspect, the antibody is, or derived from, a human, murine (e.g., mouse and rat), donkey, sheep, rabbit, goat, guinea pig, camel, horse, or chicken. Further, such antibody may be a humanized version of an antibody. The antibody may be monospecific, bispecific, trispecific, or of greater multispecificity. The antibody herein specifically include a "chimeric" antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

Examples of antibodies which can be incorporated into compositions and methods disclosed herein include, but are not limited, to antibodies such as trastuzumab (anti-HER2/neu antibody); Pertuzumab (anti-HER2 mAb); cetuximab (chimeric monoclonal antibody to epidermal growth factor receptor EGFR): panitumumab (anti-EGFR antibody); nimotuzumab (anti-EGFR antibody); Zalutumumab (anti-EGFR mAb); Necitumumab (anti-EGFR mAb); MDX-210 (humanized anti-HER-2 bispecific antibody); MDX-210 (humanized anti-HER-2 bispecific antibody); MDX-447 (humanized anti-EGF receptor bispecific antibody); Rituximab (chimeric murine/human anti-CD20 mAb); Obinutuzumab (anti-CD20 mAb); Ofatumumab (anti-CD20 mAb); Tositumumab-1131 (anti-CD20 mAb); ibritumomab tiuxetan (anti-CD20 mAb); Bevacizumab (anti-VEGF mAb); Ramucirumab (anti-VEGFR2 mAb); Ranibizumab (anti-VEGF mAb); Aflibercept (extracellular domains of YEGFR1 and VEGFR2 fused to IgG1 Fc): AMG386 (angiopoietin-1 and -2 binding peptide fused to IgG1 Fc); Dalotuzumab (anti-1GF-1R mAb): Gemtuzumab ozogamicin (anti-CD33 mAb); Alemtuzumab (anti-Campath-1/

CD52 mAb); Brentuximab vedotin (anti-CD30 mAb); Catumaxomab (bispecific mAb that targets epithelial cell adhesion molecule and CD3); Naptumomab (anti-5T4 mAb); Girentuximab (anti-Carbonic anhydrase ix): or Farletuzumab (anti-folate receptor). Other examples include antibodies such as Panorex™ (17-1 A) (murine monoclonal antibody); Panorex (@ (17-1 A) (chimeric murine monoclonal antibody); BEC2 (ami-idiotypic mAb, mimics the GD epitope) (with BCG): Oncolym (Lym-1 monoclonal antibody); SMART M 1 95 Ab, humanized 13' 1 LYM-1 (Oncolym), Ovarex (B43.13, anti-idiotypic mouse mAb); 3622W94 mAb that binds to EGP40 (17-1 A) pancarcinoma antigen on adenocarcinomas; Zenapax (SMART Anti-Tac (IL-2 receptor); SMART MI 95 Ab, humanized Ab, humanized); NovoMAb-G2 (pancarcinoma specific Ab): TNT (chimeric mAb to histone antigens); TNT (chimeric mAb to histone antigens); GJiomab-H (Monoclonals—Humanized Abs); GN1-250 Mab; EMD-72000 (chimeric-EGF antagonist); LymphoCide (humanized IL.L.2 antibody); and MDX-260 bispecific, targets GD-2, ANA Ab, SMART IDiO Ab, SMART ABL 364 Ab or ImmuRAIT-CEA.

Various methods have been employed to produce antibodies. Hybridoma technology, which refers to a cloned cell line that produces a single type of antibody, uses the cells of various species, including mice (murine), hamsters, rats, and humans. Another method to prepare an antibody uses genetic engineering including recombinant DNA techniques. For example, antibodies made from these techniques include, among others, chimeric antibodies and humanized antibodies. A chimeric antibody combines DNA encoding regions from more than one type of species. For example, a chimeric antibody may derive the variable region from a mouse and the constant region from a human. A humanized antibody comes predominantly from a human, even though it contains nonhuman portions. Like a chimeric antibody, a humanized antibody may contain a completely human constant region. But unlike a chimeric antibody, the variable region may be partially derived from a human. The nonhuman, synthetic portions of a humanized antibody often come from CDRs in murine antibodies. In any event, these regions are crucial to allow the antibody to recognize and bind to a specific antigen.

In one embodiment, a hybridoma can produce a chimeric targeted/immunomodulatory fusion polypeptide comprising a tumor targeting moiety and an immunomodulatory moiety. In one embodiment, a tumor targeting moiety comprising an antibody, antibody fragment, or polypeptide is linked or fused to an immunomodulatory moiety consisting of a polypeptide, with a linker or without a linker. The linker can be an amino acid linker. In one embodiment, a linker is (GGGGS)n wherein n is 1, 2, 3, 4, 5, 6, 7, or 8. For example, GGGGSGGGGSGGGGS (SEQ ID NO: 4). In various aspects, the length of the linker may be modified to optimize binding of the tumor target moiety or the function of the immunomodulatory moiety. In various aspects, the immunomodulatory moiety is a polypeptide that is fused to the C-terminus of the Fc region of the heavy chain of a targeting antibody or Fc-containing fusion protein. In another aspect, the immunomodulatory moiety is a polypeptide that is fused to the C-terminus of the light chain of a targeting antibody.

An antibody fragment can include a portion of an intact, antibody, e.g. including the antigen-binding or variable region thereof. Examples of antibody fragments include Fab, Fab', F(ab')2, and Fv fragments; Fc fragments or Fc-fusion products; diabodies; linear antibodies; single-chain antibody molecules; and multispecific antibodies formed from antibody fragment(s). An intact antibody is one which includes an antigen-binding variable region as well as a light chain constant domain (CL) and heavy chain constant domains, CHI, CH2 and CH3. The constant domains may be native sequence constant domains (e.g., human native sequence constant domains) or amino acid sequence variant thereof tor any other modified Fc (e.g. glycosylation or other engineered Fc).

The chimeric targeted/immunomodulatory fusion proteins of the present invention may be synthesized by conventional techniques known in the art, for example, by chemical synthesis such as solid phase peptide synthesis. Such methods are known to those skilled in the art. In general, these methods employ either solid or solution phase synthesis methods, well known in the art. Specifically, the methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups and any solid support are removed either sequentially or concurrently to afford the final polypeptide. By simple modification of this general procedure, it is possible to add more than one amino acid at a time to a growing chain, for example, by coupling (under condition that do not racemize chiral centers) a protected tripeptide with a properly protected dipeptide to form, after deprotection, a pentapeptide.

Typical protecting groups include t-butyloxycarbonyl (Boc), 9-fluorenylmethoxycarbonyl (Fmoc), benxyloxycarbonyl (Cbz), p-toluenesulfonyl (Tos); 2,4-dinitrophenyl, benzyl (Bzl), biphenylisopropyloxy-carboxycarbonyl, cyclohexyl, isopropyl, acetyl, o-nitrophenyl sulfonyl, and the like. Of these, Boc and Fmoc are preferred.

Typical solid supports are generally cross-linked polymeric materials. These include divinylbenzene cross-linked styrene-based polymers, for example, divinylbenzene-hydroxymethylstyrene copolymers, divinylbenzene-chloromethylstyrene copolymers, and divinylbenzene-benzhydryl aminopolystyrene copolymers. The divinylbenzene-benzhydrylaminopolystyrene copolymers, as illustrated herein using p-methyl-benzhydrylamine resin, offers the advantage of directly introducing a terminal amide functional group into the peptide chain, which function is retained by the chain when the chain is cleaved from the support.

In one method, the chimeric targeted/immunomodulatory fusion polypeptides are prepared by conventional solid phase chemical synthesis on, for example, an Applied Biosystems, Inc. (ABI) 430A peptide synthesizer using a resin that permits the synthesis of the amide peptide form and using t-Boc amino acid derivatives (Peninsula Laboratories, Inc.) with standard solvents and reagents. Polypeptides containing either L- or D-amino acids may be synthesized in this manner. Polypeptide composition is confirmed by quantitative amino acid analysis and the specific sequence of each peptide may be determined by sequence analysis.

Preferably, the chimeric targeted/immunomodulatory fusion polypeptides can be produced by recombinant DNA techniques by synthesizing DNA encoding the desired polypeptide. Once coding sequences for the desired polypeptides have been synthesized or isolated, they can be cloned into any suitable vector for expression. Numerous cloning vectors are known to those of skill in the art, and the selection of an appropriate cloning vector is a matter of choice. The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. Heterologous leader sequences can be added to the coding sequence that causes the secretion of the expressed polypeptide from the host organism. Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

The expression vector may then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, HEK293, baby hamster kidney (BHK) cells, monkey kidney cells (COS), human hepatocellular carcinoma cells (e.g., Hep G2), Madin-Darby bovine kidney ("MDBK") cells, NOS cells derived from carcinoma cells, such as sarcoma, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*. The proteins may also be expressed in Trypanosomes.

Depending on the expression system and host selected, the chimeric targeted/immunomodulatory fusion proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art. Once purified, the amino acid sequences of the proteins can be determined, i.e., by repetitive cycles of Edman degradation, followed by amino acid analysis by HPLC. Other methods of amino acid sequencing are also known in the art.

Once synthesized or otherwise produced, the inhibitory activity of a candidate polypeptide can be tested by assessing the ability of the candidate to inhibit the lipopolysaccharide-induced nuclear translocation of NF-KB by, for example, using murine endothelial cells.

The targeted/immunomodulatory fusion proteins of the present invention can be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular cancer type targeted. The compositions also preferably include pharmaceutically acceptable vehicles, carriers or adjuvants, well known in the art, such as human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, dextrose, glycerol, ethanol, or the like, and combinations thereof. Actual methods of preparing such compositions are known, or will be apparent, to those skilled in the art. See, e.g., Remington's Pharmaceutical Sciences, Mack Publishing Company, Easton, Pa., 18th edition, 1990.

The above compositions can be administered using conventional modes of delivery including, but not limited to, intravenous, intraperitoneal, oral, intralymphatic, or subcutaneous administration. Local administration to a tumor in question, or to a site of inflammation, e.g., direct injection into an arthritic joint, will also find use with the present invention.

The present invention provides a method of therapy involving dosing of a combination of an anti-PD-L1 antibody and the chimeric targeted/immunomodulatory fusion polypeptide of the present invention in a human patient comprising administering to the patient a first dose of the combination and followed by at least one subsequent dose of the combination, wherein the first dose and subsequent dose are separated from each other in time by at least about a few days to a few weeks to a few months. The dosage of the combination may range from about 2 mg/kg to about 16 mg/kg, e g from about 4 mg/kg to about 12 mg/kg, and optionally from about 6 mg/kg to about 12 mg/kg. An escalating dosage regimen may include a stepwise increase for the patient to receive an optimum dosage of each component that results in a partial or complete response in the patient. In the alternative, therapeutically effective doses will be easily determined by one of skill in the art and will depend on the severity and course of the disease, the patient's health and response to treatment, and the judgment of the treating physician.

EXPERIMENTAL

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1 Production of the Chimeric Targeted/Immunomodulatory Fusion Polypeptides of the Present Invention The host cell line used for the expression of recombinant targeted/immunomodulatory fusion protein expression is CHO cells or the derivative of the CHO cells. The CHO cells referred here is either freedom CHO-S cells; CHO-S Cells are CHO-derived cells adapted to high density, serum-free suspension culture in chemically-defined medium that are capable of producing high levels of secreted, recombinant protein or CHO K1 cells; having the same as ATCC No. CCL-61. It is basically an adherent cell line. The vectors used for stable cell line include the Freedom pCHO 1.0 vector, designed by ProBioGen AG, to express one or two genes of interest downstream of the vector's two different hybrid CMV promoters. This vector contains the dihydrofolate reductase (DHFR) selection marker and a puromycin resistance gene, allowing selection using MTX and Puromycin simultaneously.

The light chain fusion protein coding nucleic acid sequences are cloned into the restriction enzyme sites AvrII and BstZ17 under the control of EF2/CMV promoter. The heavy chain fusion protein coding nucleic acid sequences are cloned, in restriction enzyme sites EcoRV and PacI under the control of CMV/EF1 promoter. The construct(s) are transfected into Freedom CHO-S cells/CHOK1 cells. The high producer single, clonal cell strain is selected for producing the recombinant targeted/immunomodulatory fusion protein. Prepare the MCB and characterize for cell viability, productivity, stability and other parameters. The cells are used for culturing followed by purification.

The cell culture is performed in feed-batch mode. In the cell culture, the mammalian host cells used is Chinese Hamster Ovary (CHO) cells and culture medium are supplied initially. The CHO cells are genetically engineered to produce the targeted/immunomodulatory fusion protein. The zinc sulphate hepta hydrate salt is added in the medium at a concentration of 0.4 mM. In contrast, there is no addition of any zinc salt in the control medium. The production fermentation run starts with an initial cell count of 0.3-0.45× $10^6$ cells/ml at 37±1° C., the first 3-4 days are dedicated to grow the cells in batch phase. Next step involves lowering the temperature to 31±1° C. and continuing the run till 7th day. Lactate reduces by almost 10-40% throughout the run. The produced targeted/immunomodulatory fusion protein is then collected from the media using the technique of affinity chromatography.

Purification of antibody-peptide fusion immunostimulatory molecules using protein A column. Supernatant culture secreted from recombinant CHO cell line containing the fusion monoclonal antibodies is tested for titer and endotoxins under sterile conditions. The supernatant is subjected to affinity chromatography using Mab Select Xtra Protein A affinity resin, washed and equilibrated with binding buffer. The pH of the supernatant is adjusted using 0.5 M phosphate to the same pH as the column; the supernatant is allowed to bind to the column/pass through the column at the flow rate of 0.5 ml/minute to achieve the maximum binding. All the antibody-proteins fusion molecules bind through the Fc region while impurities are eliminated as flow through. The column is washed with equilibration buffer and the bound fusion molecules are eluted using 0.1 M glycine at pH 3.0. The pH of the eluted proteins is adjusted to neutral pH or the stable formulation pH and the purified protein are stored at −20° C. or at 2-8° C.

Example 2 Testing of the FmAb2 Antibody in Combination with Anti-PD-L1 Antibody FmAb2 is a recombinant fusion monoclonal antibody consisting of transforming growth factor receptor II extracellular domain fused to an anti-EGFR monoclonal antibody at the C-terminus of the light chain via a 15 amino acid linker. The theoretical molecular weight of FmAb2 is 178.10 KDa. Each heavy chain has 448 (lacking an end lysine on C-terminus) amino acids and each light chain along with the linker and TGFβRII has 366 amino acids as shown in FIG. 3.

FmAb2 is secreted as an intact targeted/immunomodulatory fusion protein. Anti EGFR arm of FmAb2 antibody binds to EGFR expressed on the tumor cells resulting in inhibition of tumor cell proliferation. TGFβRII-ECD arm binds to the circulating TGFβ1 and therefore neutralizes its tumorigenic effect and enhances immune activity. In human PBMCs based stimulation assay, the effect of FmAb2 antibody has been evaluated on T cells proliferation and cytokine release such as IFNγ and TGFβ1. Anti PD-L1 antibody blocks the inhibitory interaction of PD-1 (present on T cells) with its ligand PD-L1 (present on tumor cells and antigen presenting cells) and therefore enhances immune response. PD-L1 overexpression is one of the immune escape mechanisms shown by EGFR expressing tumors suggesting an important role of anti PD-L1 monoclonal antibody in combination with FmAb2 for further enhanced immune response.

The present invention includes evaluation of functional activity of FmAb2 on T cell activation and cytokine secretion/trapping (IFNγ and TGFβ1) using Human PBMCs based stimulation assays. Soluble anti-CD3 (OKT3 clone) can stimulate T cells present in human PBMCs resulting in their activation and proliferation. Activated T cells secrete cytokines like interferon gamma (IFNγ) and interleukins to perform effector cell function. In this assay, TGFβRII-ECD arm of FmAb2 is evaluated, wherein, it traps the TGFβ1 which is secreted in human PBMC cultures by monocytes and macrophages. The cytokine is also supplemented externally by fetal bovine serum present in complete growth media which is required for culture of cells in invitro assays. In another set of experiments, exogenous TGFβ1 was added and role of TGFβRI IECD arm was evaluated. Importantly it was found that TGFβRII ECD traps inhibitory TGFβ1 and results in immune activation which is observed as enhanced IFNγ secretion. Anti PD-L1 antibody blocks the inhibitory PD-1 (PD-1 on T cells) and PD-L1 (PD-L1 on antigen presenting cells/activated T cells) interaction results in an increase in IFNγ secretion due to immune activation. Notably and surprisingly, this immune activation, shows even further increase, when anti PD-L1 is added in combination with FmAb2 antibody causing an overall increase in IFNγ secretion due to immune activation by anti PD-L1 antibody and TGFβ1 neutralization by FmAb2 antibody.

Procedure to Evaluate Effect of FmAb2 Antibody on Cytokine Release (IFNγ/TGFβ1) by Stimulated Human PBMCs in the Presence or Absence of Spiked TGFβ1:

Day 0: Human PBMCs were revived in RPMI complete media/Tex MACS media a day before performing the assays and were incubated overnight at 37° C. in cell culture flasks.

Day 1: The cells were harvested from cell culture flasks and transferred to centrifuge tubes, centrifuged at 1000 RPM, 5 min, 21° C. Supernatant was discarded, and the pellet was re-suspended in RPMI complete media or in Tex MACS media. Cell count was performed using trypan blue cell viability dye and the counts were adjusted to 2 million cells/mL. 50 µL of the above cell density was seeded per well to reach the final cell numbers as 0.1 million cells/well. Alternatively, in few experiments, 100 µL of 2.5 million cells/mL and 1.0 million cells/mL were seeded per well to reach the final cell numbers as 0.25 million cells/well and 0.1 million cells/well.

Soluble anti-CD3 antibody (OKT3 clone) was added at varied concentrations of 2, 1, 0.5 and/or 0.25 ng/mL. (Concentration used in specific experiments are mentioned in the figures legend). 4× of the required final concentration was prepared and 50 μL was added per well.

Recombinant Human TGFβ1 was added at a final concentration of 100, 10, 5, 2.5, 1, 1.25, 0.1 ng/mL. (Concentration used in specific experiments are mentioned in the figure legend). 4× of the required final concentration was prepared and 50 μL was added per well.

4× concentration of FmAb2/isotype antibody was prepared and 50 μL was added per well to get a final concentration of 10 μg/mL. In some experiments, FmAb2 antibody/TGFβRII ECD was added at a final concentration of 56.18 nM, 5.618 nM, 0.5618 nM and 0.05618 nM and isotype antibody (cetuximab) was added at a final concentration of 56.18 nM. (Concentration used in specific experiments are mentioned in the figure legend).

The final well volume was adjusted to 200 μL using RPMI complete media or in Tex MACS media. The plates were incubated for 3 days at 37° C., 5% CO2 and the final readout was taken in the form of cytokine ELISA (IFNγ/TGFβ1).

FIG. 4 shows the release of IFNγ by stimulated Human PBMCs (anti CD3 added at 2 ng/mL) in the presence of FmAb2 antibody added at a titrating concentration. The graph also includes the data from combination of FmAb2 with anti PD-L1 antibody (Atezolizumab) (SEQ ID NOs. 10 (heavy chain) and 11 (light chain)). Data is plotted as Mean±SD of triplicates. It is representative graph of four independent experiments. The exogenous addition of TGFβ1 showed reduction in secretion levels of IFNγ. Addition of FmAb2 antibody resulted in an increase in IFNγ secretion levels in a dose dependent manner. Importantly, this increase in IFNγ secretion was further enhanced by addition of anti PD-L1 antibody along with FmAb2.

Figure 5:
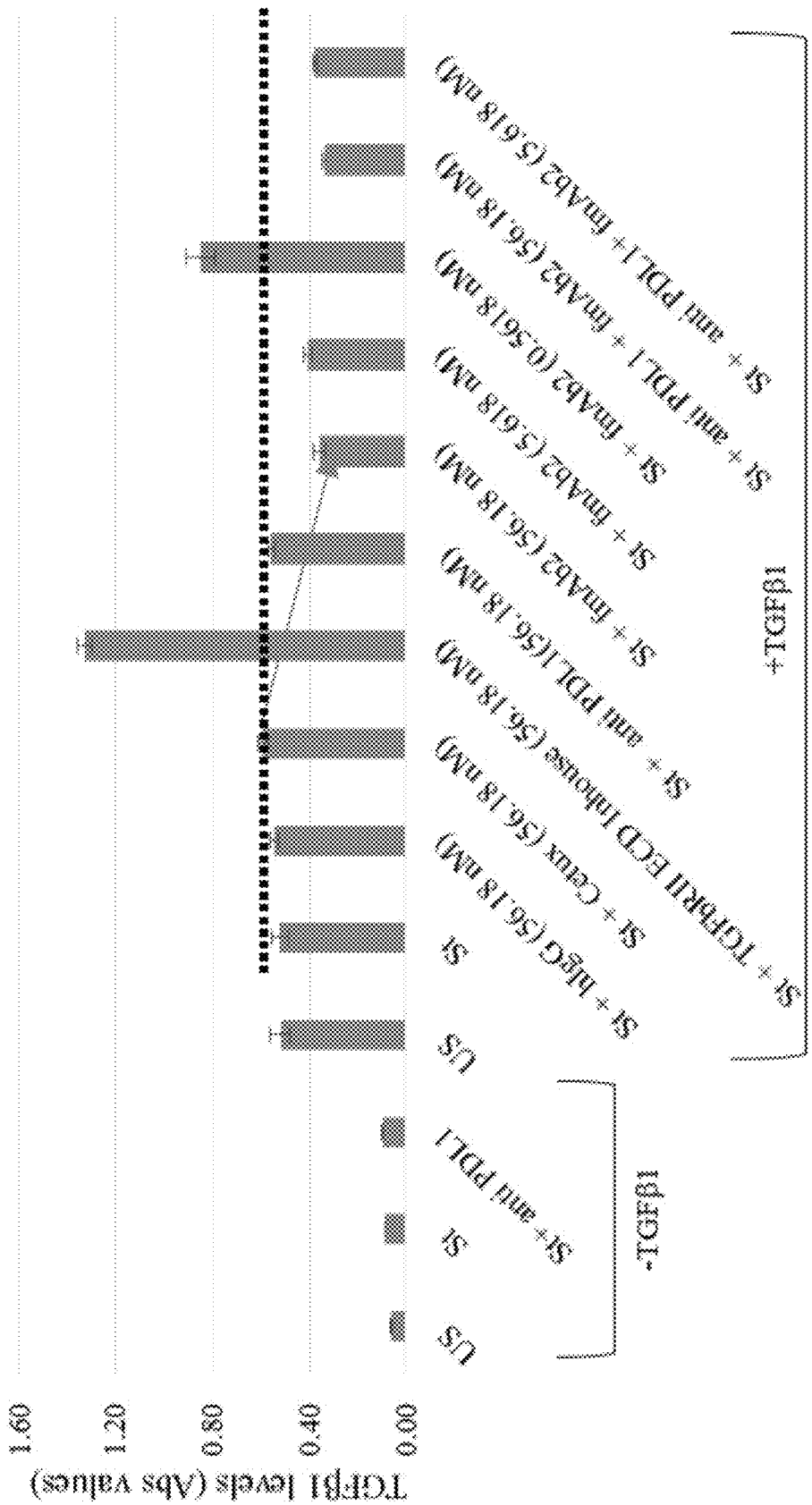
FIG. 5 The above graph shows TGFβ1 trapping by FmAb2 antibody added at a titrating concentration to stimulated (st) Human PBMCs (anti CD3 added at 2 ng/mL). The graph also includes the data from the combination of FmAb2 with anti PD-L1 antibody.

FIG. 5 shows the trapping of TGFβ1 by adding the FmAb2 antibody at a titrating concentration to stimulated Human PBMCs (anti CD3 added at 2 ng/mL). The graph also includes the data from combination of FmAb2 with anti PD-L1 antibody. Data is plotted as Mean±SD of triplicates. It is representative graph of four independent experiments. It was shown that in presence of FmAb2 antibody reduced levels of TGFβ1 were observed. This reduction was observed in a dose dependent manner. Also, it was noticed that FmAb2 at lower concentration did not show neutralization of TGFβ1, instead an increase in TGFβ1 levels was observed. Therefore, to understand the same, a dose dependent external spiking of TGFβ1 was performed at 100, 10, 1 and 0.1 ng/mL to assess the levels for IFNγ and TGFβ1 in the milieu.

Figure 6:
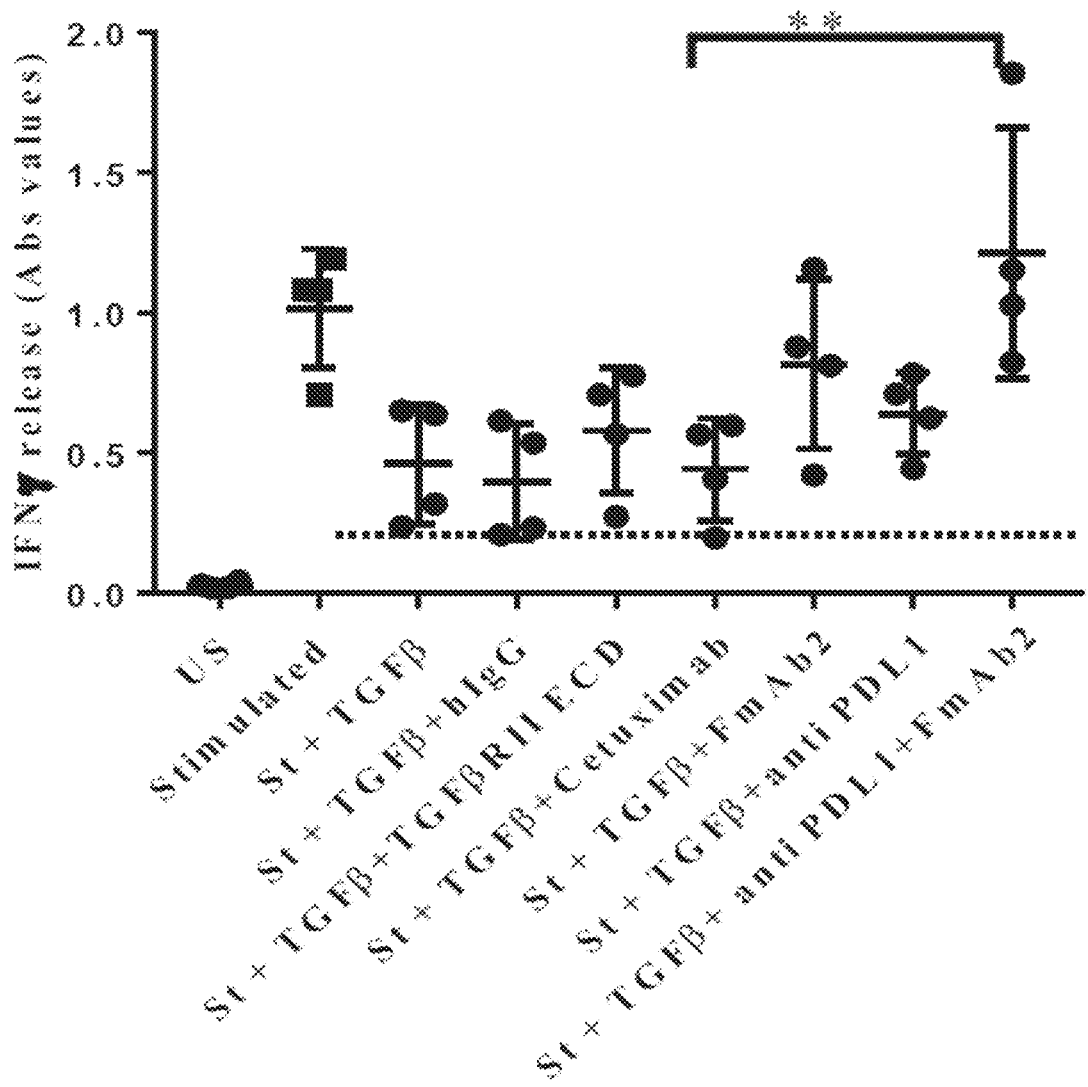
FIG. 6 shows compilation of data to show the surprising and synergistic effects of the combination of FmAb2 and anti PD-L1 antibody on IFNγ release by stimulated Human PBMCs.

FIG. 6 shows a compilation of data showing the effect of combination of FmAb2 and anti PD-L1 antibody on IFNγ release by stimulated Human PBMCs. The antibodies were added at equimolar concentration of 56 nM. Each point represents an independent experiment (triplicate value for individual treatment group). The data is plotted as Mean±SD of all runs within the treatment groups. It was observed that the addition of FmAb2 and anti PD-L1 antibody in combination showed a significant enhancement in IFNγ secretion levels over Cetuximab group (Analyzed using One Way ANOVA, non-parametric, Kruskal Wallis test, p value=0.0089). Further, the data showed more robust and consistent response of test antibodies in TGFβ1 spiked condition as compared to the non-spiked experiments. Therefore, extensive studies were performed in TGFβ1 spiked format. In stimulated human PBMCs, addition of TGFβ1 reduced IFNγ secretion. This inhibition remained same even when the concentration of TGFβ1 was varied from 10 to 1.25 ng/mL.

Effect of FmAb2 antibody on IFNγ and TGFβ1 levels was evaluated in the cell supernatants (collected 72 hours post stimulation) from these assays. The antibody was able to show enhanced IFNγ secretion over stimulated group in a dose dependent manner indicating enhanced T cell activation due to trapping of inhibitory TGFβ1 (FIGS. 4-5).

Synergy of FmAb2 and anti PD-L1 antibody was observed when used in stimulated PBMC cultures, wherein the addition of anti PD-L1 antibody showed an enhanced IFNγ secretion by blocking the inhibitory PD-1 (on T cells) and PD-L1 (on APCs and activated T cells in PBMC milieu) interaction. Upon exogenous addition of TGFβ1, this immune activating function of anti PD-L1 antibody was partially reduced as measured by IFNγ secretion. This suggests that blocking the inhibitory PD-1/PD-L1 interaction was not sufficient in the presence of inhibitory role of TGFβ1, to cause complete immune activation. However, and importantly, the addition of FmAb2 (with TGFβ trap) and PD-L1 antibody in combination, showed complete rescue from immune suppression by dual targeting of inhibitory molecules (i.e blocking PD-1/PD-L1 inhibitory interaction as well as mopping off inhibitory TGFβ1) (FIG. 6).

In conclusion, data from multiple runs clearly indicate that FmAb2 enhances IFNγ secretion in a dose dependent manner even in the presence of exogenously spiked TGFβ1. Hence it is reasonable to conclude that FmAb2 antibody enhances T cell activation (as indicated by increase in IFNγ level) by trapping the TGFβ1. Further, the combination of FmAb2 and anti PD-L1 antibodies in PBMC immune assays showed complete rescue from immune suppression by dual targeting of inhibitory molecules. Considering the expression of PD-L1 on tumors as a mechanism of immune escape, this data suggests a very important therapeutic role of using FmAb2 and anti PD-L1 antibody as combination therapy in patients with higher EGFR expressing tumors. This combination has the therapeutic advantage of delaying and/or preventing the development of resistance to EGFR mediated therapeutics.

Although the invention has been described with reference to the above example, it will be understood that modifications and variations are encompassed within the spirit and scope of the invention. Accordingly, the invention is limited only by the following claims.

Abbreviations

PBMC-Peripheral Blood Mononuclear Cells; SOP-Standard Operating Procedure; CV-Coefficient of Variance; wrt-With respect to; RPMI-Roswell Parker Memorial Institute; FBS-Fetal bovine serum; IFNγ-Interferon Gamma; TGF-β1-Transforming growth factor beta; EGFR-Epidermal Growth Factor Receptor; TGFβRII ECD/TGFβ trap-Transforming Growth Factor Beta Receptor Type 2 Extra Cellular Domain; IRS-Internal Reference Standard; DDL-Drug Discovery Lab; DOA-Date of assay readout(ELISA); RPM-Revolutions per minute; US-Unstimulated, St-Stimulated with anti CD3.

That which is claimed is:

1. A method of immunotherapy, the method comprising contacting cells with a composition comprising a therapeutically effective amount of an anti-PD-L1 antibody that binds to PD-L1 and having binding activity to PD-1 to block the inhibitory interaction of PD-1 with PD-L1 and a chimeric targeted/immunomodulatory fusion polypeptide comprising an immunomodulatory moiety that binds transforming growth factor beta (TGF-β) and a tumor targeting moiety that binds to EGFR1, wherein the chimeric targeted/immunomodulatory fusion polypeptide consists of SEQ ID NO: 1 and 9, wherein the anti-PD-L1 antibody comprises SEQ ID NOs: 10 and 11 and wherein the composition increases IFNγ secretion and neutralization of TGFβ1 in the cells.

2. The method of claim 1, wherein the composition comprising a therapeutically effective amount of an anti-PD-L1 antibody and the chimeric targeted/immunomodulatory fusion polypeptide increases TGF-β1 trapping in the cells.

3. The method according to claim 1, wherein the anti-PD-L1 antibody and the chimeric targeted/immunomodulatory fusion polypeptide are introduced sequentially in either order or simultaneously.

4. The method according to claim 1, wherein the cells are in a human subject.

* * * * *